United States Patent
Bealin-Kelly et al.

(10) Patent No.: US 6,432,441 B1
(45) Date of Patent: Aug. 13, 2002

(54) THROAT SOOTHING COMPOSITIONS

(75) Inventors: Francis Joseph David Bealin-Kelly, Surrey (GB); Bernhard Hanke, Bad Schwalbach; Paul Nienaber, Ingelheim, both of (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/403,375

(22) PCT Filed: Apr. 14, 1998

(86) PCT No.: PCT/IB98/00553
§ 371 (c)(1), (2), (4) Date: Oct. 20, 1999

(87) PCT Pub. No.: WO98/47482
PCT Pub. Date: Oct. 29, 1998

(30) Foreign Application Priority Data

Apr. 21, 1997 (GB) ............................................. 9707978

(51) Int. Cl.[7] .......................... A61K 9/68; A61K 47/00; A61K 9/20; A23K 3/00; A23G 3/00
(52) U.S. Cl. ........................ 424/440; 424/439; 424/441; 424/464; 426/3; 426/321; 426/660
(58) Field of Search .................................. 424/439, 440, 424/464, 441; 426/3, 321, 660

(56) References Cited

U.S. PATENT DOCUMENTS

| | | | |
|---|---|---|---|
| 3,894,154 A | 7/1975 | Graff et al. ................... 426/5 |
| 4,136,163 A | 1/1979 | Watson et al. ................. 424/54 |
| 4,157,402 A | 6/1979 | Ogawa et al. .................. 426/5 |
| 4,230,688 A | 10/1980 | Rowsell et al. ............... 424/45 |
| 4,250,196 A | 2/1981 | Friello ........................ 426/5 |
| 4,372,842 A * | 2/1983 | Cimiluca ..................... 424/16 |
| 4,372,942 A | 2/1983 | Cimiluca ..................... 424/16 |
| 4,466,983 A | 8/1984 | Cifrese et al. ................ 426/5 |
| 4,517,205 A * | 5/1985 | Aldrich ...................... 426/103 |
| 4,762,719 A | 8/1988 | Forester ..................... 424/440 |
| 4,774,094 A * | 9/1988 | Carroll et al. ................ 426/3 |
| 4,980,169 A * | 12/1990 | Oppenheimer et al. ....... 424/439 |
| 5,002,791 A | 3/1991 | Knebl ........................ 426/660 |
| 5,458,894 A | 10/1995 | Knebl et al. ................. 426/231 |
| 5,912,007 A | 6/1999 | Pan et al. | |

FOREIGN PATENT DOCUMENTS

| | | |
|---|---|---|
| EP | 0140085 | 9/1984 |
| EP | 0431376 | 11/1990 |
| EP | 0534823 | 9/1992 |
| GB | 1452291 | 8/1973 |
| WO | WO 9702273 | 1/1997 |
| WO | WO 9706695 | 2/1997 |

* cited by examiner

*Primary Examiner*—Thurman K. Page
*Assistant Examiner*—S. Tran
(74) *Attorney, Agent, or Firm*—Joan B. Cunningham; Betty J. Zea; Karen F. Clark

(57) ABSTRACT

A throat drop comprises from 60% to 95% of an edible shell and from 5% to 40% of an aqueous filling, by weight of the drop. The filling contains a throat relief agent, from 8% to 95%, by weight, water and from 0.001% to 10%, by weight, of a vesicle-forming agent which encapsulates the throat relief agents with vesicles which are dispersed within the filling. The vesicles have a number average particle size of from about 1 to about 100 μm.

30 Claims, No Drawings

THROAT SOOTHING COMPOSITIONS

This application is a 371 of PCT/LB 98/00553 field Apr. 14, 1998

FIELD OF THE INVENTION

The present invention relates to orally ingestible compositions, especially liquid centre-filled confectionery compositions, for soothing of sore or irritated throats and relief of congested nasal passages.

BACKGROUND OF THE INVENTION

Products in the form of cough drops have long been known as vehicles for the delivery of medicaments aimed at soothing sore or irritated throats. Such medicaments include analgesics, antitussives, expectorants, cooling agents such as menthol, and warming agents such as ethanol or gingerol. The medicament can be administered by way of a throat drop or lozenge which releases the active agent upon sucking. Particularly in the case of a volatile active agent, the product can also provide relief from cold symptoms by way of clearing the nasal passages.

EP-A-431,376, for example, describes hard confections for sustained release treatment of sore throats comprising hydrogenated isomaltulose and an active ingredient which can be an antitussive or antihistamine but can also be a volatile oil such as menthol or eucalyptus. The confection normally contains a further flavouring agent such as lemon, honey or cherry but which can also be menthol or eucalyptus.

One of the problems faced in delivering long-lasting relief from such a product is maintaining the active ingredient in the throat for a sufficiently long period of time. It has now been found, however, that encapsulating the active ingredient within vesicles can act significantly to prolong the throat relief delivered by the active.

Lecithins are well known as food emulsifiers and they have also been disclosed as e.g. humectants. U.S. Pat. No. 4,250,196, for example, discloses a liquid centre-filled chewing gum where lecithin is one of many optional humectants in the centre-fill portion. U.S. Pat. No. 4,466,983 discloses substantially non-aqueous semi-liquid centre-fill products in which one of the examples employs lecithin as an emulsifier. Lecithins have also been used to form vesicles for the delivery of drugs, as disclosed for example in EP-A-140,085. However, it is believed that it has not previously been recognised that vesicles, encapsulating a throat soothing active, can be incorporated into a medicated confectionery composition to deliver a prolonged soothing effect in the throat and nasal passages.

It is accordingly an object of this invention to provide medicated confectionery compositions, especially throat drops, delivering prolonged throat and nasal soothing.

SUMMARY OF THE INVENTION

The present invention relates to a throat drop comprising from 60 to 95%, preferably from 75 to 85%, of an edible shell and from 5 to 40%, preferably from 15 to 25%, of an aqueous filling, by weight of the drop, the filling comprising from 8 to 95% water and from 0.001 to 10% of a vesicle-forming agent which encapsulates the throat relief agent within vesicles which are dispersed within the filling.

All levels and ratios are by weight, unless otherwise indicated. Percentages are by weight of the filling unless otherwise specified.

DETAILED DESCRIPTION OF THE INVENTION

The present invention provides a throat drop comprising a throat relief agent encapsulated within vesicles. Without wishing to be bound by theory, it is believed that the vesicles acts as a bioadhesive and are able to sustain the throat relief agent within the throat, giving a prolonged throat soothing effect. The vesicles are suspended within an aqueous filling encased in an edible shell. By 'throat drop' is meant a medicated confection which is suitable for sucking or chewing within the mouth, thereby releasing the throat relief agent.

The aqueous filling comprises water, generally at a level of from about 8 to about 95%, but preferably from about 8 to about 20%, more preferably from about 10 to about 15% by weight of the filling. Levels of water higher than about 20% are unsuitable for the production of centre-filled hard candies. The filling can be a liquid, gel or paste.

An essential component of the throat drops of the present invention is a throat relief agent. By "throat relief agent" herein is meant any organic compound or mixture of compounds capable of providing relief to a person with a sore or irritated throat or nasal passage. Classes of throat relief agents include, but are not limited to analgesics, antitussives, expectorants, physiological cooling agents, physiological warming agents and mixture thereof. Preferably the throat relief agent is selected from physiological cooling agents, physiological warming agents and mixtures thereof. Suitable levels of the throat relief agent are from about 0.001 to about 10%, preferably from about 0.01 to about 5%, more preferably from about 0.05 to about 3% by weight of the aqueous composition.

Suitable physiological cooling agents are described in WO97/06695, incorporated by reference herein. Preferred for use herein are physiological cooling agents selected from the group consisting of menthol, peppermint oil, N-substituted-p-menthane-3- carboxamides, acyclic tertiary and secondary carboxamides, 3-1-menthoxy propan-1,2-diol and mixtures thereof. Particularly preferred for use herein are menthol and menthol containing oils such as peppermint oil.

The carboxamides found most useful are those described in U.S. Pat. No. 4,136,163, Jan. 23, 1979 to Watson et al., and U.S. Pat. No. 4,230, 688, Oct. 28, 1980 to Rowsell et al. The carboxamides in U.S. Pat. No. 4,136,163 are N-substituted-p-menthane-3-carboxamides. N-ethyl-p-menthane-3-carboxamide, commercially available as WS-3 from Wilkinson Sword, is preferred herein. The carboxamides of U.S. Pat. No. 4,230,688 are certain acyclic tertiary and secondary carboxamides, of which trimethyl isopropyl butanamide, commercially available as WS-23 from Wilkinson Sword is preferred for use herein.

Preferred physiological warming agents are those selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amylalcohol, benzyl alcohol, chloroform, eugenol, cinnamon oil, cinnanic aldehyde, and phosphate derivatives thereof. The phosphate derivatives are those described in WO 97/02273, incorporated by reference herein.

The throat drops of the present invention also comprise from 0.001 to 10% by weight of the filling of a vesicle-forming agent which acts to form vesicles which are dispersed within the filling and encapsulate the throat relief agent. By 'vesicle' is meant an essentially spherical structure comrprising a lipid bilayer encapsulating a central core. The vesicles herein can be uni- or multi-lamellar and have a number average particle size of from about 1 to about 100 $\mu$m, more preferably from about 5 to about 50 $\mu$m. The particle size can be measured using an optical microscope, such as a Nikon Optiphoto 2, linked to an electronic image analysis system such as the Linkam MS100. Measurement can also be made using a graduated graticule in the field of view. EP-A-534,823, which describes anhydrous make-up compositions which can form vesicles on exposure to water gives a comprehensive list of amphiphilic liquids which can be used to form vesicles. For the throat drops herein it is of course preferable that food-grade materials are used and the preferred vesicle forming agents are natural phospholipids such as egg or soy lecithin. The preferred phospholipids of the present invention are plant-derived lecithins and, especially, soybean lecithin. Soybean lecithin can act to form vesicles at very low levels. Preferably the vesicle forming agent is present at a level of from about 0.001 to about 1%, more preferably from about 0.005 to about 0.1% and especially from about 0.01 to about 0.05% by weight of the filling. With adequate mixing, in the presence of water and a throat relief agent as described herein, the lecithin forms vesicles which encapsulate the throat relief agent.

It has further been found that the vesicle formation is enhanced by the presence of glycerine, which is preferably present at a level of from about 5 to about 25%, preferably from about 10 to about 20%, more preferably from about 12 to about 18% by weight of the filling.

The palatability of the filling is substantially improved if the composition further comprises a bulk sweetener, such as a sugar, suitably at a level of from about 5 to 80%, preferably from about 50 to about 75% on a dry solids basis by weight of the filling. A preferred source of the sweetener is high fructose corn syrup which, being commercially available as an 85% active material of which the balance is essentially water, can also provide some, or even all, of the water required by the aqueous filling.

Sugar free compositions comprising a sugar alcohol such as sorbitol can also be used. Preferably however, sugar alcohols are employed in admixture with glycerine, since it has been found that sugar alcohols on their own can suppress vesicle formation.

The aqueous fillings herein can also include a flavouring agent. As used herein, the term 'flavouring agent' means those flavour essences and equivalent synthetic ingredients which are added to the flavour composition for the principal purpose of providing flavour to the confectionery product. It excludes throat relief agents as described above. Flavouring agents well known in the confectionery art can be added to the flavour compositions of the invention. These flavouring agents can be chosen from synthetic flavouring liquid and/or oils derived from plants leaves, flowers, fruits and so forth, and combinations thereof. Representative flavouring liquids include: artificial, natural or synthetic fruit flavours such as lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derive flavours such as licorice. The amount of flavouring agent employed is normally a matter of preference subject to such factors as flavour type, base type and strength desired. In general, amounts up to about 4% by weight are usable with amounts of from. about 0.1% to about 1% being preferred.

The edible shell can be a chewing gum or a hard or soft candy, preferably it is a hard candy. Centre-filled chewing gums are described, for example, in U.S. Pat. No. 3,894,154. Centre-filled hard candies are described in U.S. Pat. No. 4,372,942 and U.S. Pat. No. 4,466,983. A suitable sugar base for a hard candy shell comprises from about 30% to about 85% glucose syrup and from about 15% to about 70% sucrose. Alternatively, a sugar-free base can be used for the shell. Suitable sugar-free bases include bulk sweeteners such as isomalt, maltitol and sorbitol. Isomalt and maltitol are preferred. The inner surface of the shell can also have a separate edible lining to prevent or reduce interaction of the filling. with the shell. The edible shell can also further comprise flavours and throat relief agents as described above. In preferred throat drops according to the invention both the edible shell and the liquid centre-fill comprise a throat relief agent. In this way the consumer experiences both immediate and long-lasting throat and nasal congestion relief.

The aqueous filling can be made by straightforward mixing techniques. The general techniques for manufacturing centre-filled confectionery products can be found in the "Silesia Confiserie Manual No. 3", published by Silesia-Essenzenfabrik Gerhard Hanke K. G., Abt. Fachbuicherei.

Centre-filled throat drops according to the invention can be manufactured by deposit, rope-forming and extrusion processes as known in the art. Extrusion and rope-forming processes are preferred. An example of an extrusion process is described in U.S. Pat. No. 5,458,894. An example of an extrusion process is described in U.S. Pat. No. 5,002,791.

The following examples are given to illustrate the compositions and uses according to the invention. However, the invention is not limited thereto.

EXAMPLE 1

Liquid, centre-filled throat drops were prepared according to formulae A and B below. The liquid filling was made by adding a premix of the lecithin, colour solution, flavour oils and/or cooling and warming agents to a mixture of the high fructose corn syrup pre-warmed to 82° C. The components were mixed for two minutes and co-extruded with a separately made candy base to produce centre-filled throat drops.

|  | A<br>Wt. % | B<br>Wt. % |
|---|---|---|
| Candy casing (80% by wt. of drop) | | |
| Sucrose | 58.12 | 49.37 |
| Glucose syrup (80% solids) | 41.51 | 49.37 |
| Peppermint oil | 0.17 | — |
| Menthol | 0.17 | 0.08 |
| Lemon oil | — | 0.27 |
| Citric acid | — | 0.91 |
|  | 100% | 100% |
| Liquid filling (20% by wt. of drop) | | |
| High fructose corn syrup[1] | 84.38 | 84.306 |
| Glycerine | 15.0 | 15.0 |
| Lecithin | 0.02 | 0.02 |
| Lemon oil | — | 0.314 |
| Colour (5% aqueous) | 0.32 | 0.16 |
| Peppermint oil | 0.15 | — |
| David Michael Heat[2] | 0.125 | 0.20 |
| Vanillin | 0.005 | — |
|  | 100% | 100% |

[1] 85% sugar solids, the balance being essentially water
[2] A warming agent available from David Michael & Co., Inc., Philadelphia, USA The throat drops of formulae A and B were sucked by individuals experiencing throat or nasal irritation. An immediate sensation of relief, expressed as throat soothing or nasal clearing, was noted by the individuals, which was significantly enhanced when the candy shell was broken. The sensation of relief was experienced for up to fifteen minutes after treatment.

What is claimed is:

1. A throat drop comprising, by weight of the drop, from 60% to 95% of an edible shell, and from 5% to 40% of an aqueous filling, wherein the aqueous filling comprises, by weight of the filling, from 0.001% to 10% water, and from 8% to 95% of a throat relief agent encapsulated within a vesicle-forming agent to form spherical vesicles having an average particle size of from about 1 to about 100 μm, and wherein the spherical vesicles are dispersed within the aqueous filling.

2. A throat drop according to claim 1, wherein the drop comprises from 75 to 85% of the shell and from 15 to 25% of the filling by weight of the drop.

3. A throat drop according to claim 1, wherein the filling comprises, by weight, from about 10% to about 15% water and from 0.005% to about 0.1% vesicle-forming agent.

4. A throat drop according to claim 3, wherein the filling further comprises, by weight, from about 10% to about 20%, glycerine.

5. A throat drop according to claim 1 wherein the filling further comprises from 5 to 80% sugar.

6. A throat drop according to claim 5, wherein the sugar is provided by high fructose corn syrup.

7. A throat drop according to claim 1 wherein the shell comprises a sugar-free base.

8. A throat drop according to claim 7 wherein the filling comprises a sugar alcohol.

9. A throat drop according to claim 8 wherein the sugar alcohol is in admixture with glycerine.

10. A throat drop according to claim 1 wherein the throat relief agent is selected from the group consisting of physiological cooling agents, physiological warming agents and mixtures thereof.

11. A throat drop according to claim 10 wherein the throat relief agent comprises a physiological cooling agent selected from the group consisting of menthol, peppermint oil, N-substituted-p-menthane-3-carboxamides, acyclic tertiary and secondary carboxamides, 3-1-menthoxy propan-1,2-diol, and mixtures thereof.

12. A throat drop according to claim 10 wherein the throat relief agent comprises a physiological warming agent selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amyl alcohol, beanzyl alcohol, chloroform, eugenol, cinnamon oil, cinnamic aldehyde, and phosphate derivatives thereof.

13. A throat drop according to claim 1, wherein the vesicle-forming agent comprises soybean lecithin.

14. A confection comprising:
  (a) a shell comprising sweetener, and
  (b) an aqueous filling comprising glycerine and a throat relief agent encapsulated within a vesicle-forming agent to form spherical vesicles having an average particle size of from about 1 to about 100 μm, wherein the spherical vesicles are dispersed within the aqueous filling;

wherein the throat relief agent is selected from the group consisting of analgesics, antitussives, expectorants, physiological cooling agents, physiological warming agents, and mixtures thereof.

15. A confection according to claim 14, wherein the throat relief agent is selected from the group consisting of analgesics, antitussives, expectorants and mixtures thereof.

16. A confection according to claim 14, wherein the vesicle-forming agent comprises phospholipids.

17. A confection according to claim 14, wherein the filling comprises, by weight, from about 10% to about 20% glycerine.

18. A confection according to claim 17, wherein the filling comprises vesicles having a number average particle size of from about 5 to about 50 μm.

19. A confection according to claim 17, wherein the filling further comprising from about 10% to about 15% water, and from about 0.005% to about 0.1% lecithin.

20. A method of prolonging the sensation of relief provided by a throat relief agent, comprising the steps of:
  (a) encapsulating a throat relief agent in spherical vesicles with a vesicle-forming agent to form encapsulated throat relief agent; and
  (b) forming a confection comprising a shell and an aqueous filling, wherein the filling comprises the encapsulated throat relief agent and wherein the spherical vesicles are dispersed within the aqueous filling.

21. A method according to claim 20, wherein the step of encapsulating a throat relief agent in spherical vesicles comprises mixing the throat relief agent with water and lecithin.

22. A method according to claim 21, wherein the filling comprises from about 0.001% to about 10%, by weight, throat relief agent.

23. A throat drop comprising:
(a) an edible shell comprising a first throat relief agent, and
(b) an aqueous filling comprising a second throat relief agent encapsulated within a vesicle-forming agent to form spherical vesicles having an average particle size of from about 1 to about 100 µm, wherein the spherical vesicles are dispersed within the aqueous filling.

24. A throat drop according to claim 23, wherein the vesicles-have a number average particle size of from about 5 to about 50 µm.

25. A throat drop according to claim 23, wherein the first throat relief agent comprises a cooling agent and the second throat relief agent comprises a warming agent.

26. A throat drop according to claim 23, wherein the filling comprises, by weight, from about 0.05% to about 3% throat relief agent.

27. A confection according to claim 26, wherein the filling further comprising from about 10% to about 15% water, from about 0.01% to about 0.05% phospholipid, from about 12% to about 18% glycerine, and from about 0.1% to about 1% flavouring agent.

28. A throat drop according to claim 27, wherein the phospholipid is plant derived lecithins.

29. A throat drop according to claims 28, wherein the shell comprises glucose syrup and sucrose.

30. A throat drop according to claim 23, wherein the shell comprises a sugar-free base selected from the group consisting of isomalt, maltitol, sorbitol and mixtures thereof.

* * * * *

UNITED STATES PATENT AND TRADEMARK OFFICE
CERTIFICATE OF CORRECTION

PATENT NO.    : 6,432,441 B1
DATED         : August 13, 2002
INVENTOR(S)   : Francis Joseph David Bealin-Kelly et al.

It is certified that error appears in the above-identified patent and that said Letters Patent is hereby corrected as shown below:

Column 5,
Lines 40-42, please cancel "weight of the filling, from 0.001% to 10% water, and from 8% to 95% of a throat relief agent encapsulated within a vesicle forming agent to form spherical vesicles having an" and insert therefor: -- weight of the filling, from 8% to 95% water, and a throat relief agent encapsulated within from 0.001% to 10% of a vesicle forming agent to form spherical vesicles having an --

Signed and Sealed this

Third Day of June, 2003

JAMES E. ROGAN
*Director of the United States Patent and Trademark Office*